US011226188B2

(12) United States Patent
Courteville et al.

(10) Patent No.: US 11,226,188 B2
(45) Date of Patent: Jan. 18, 2022

(54) LOW-COHERENCE REFLECTOMETRY METHOD AND DEVICE EMPLOYING TIME-FREQUENCY DETECTION

(71) Applicant: FOGALE NANOTECH, Nîmes (FR)

(72) Inventors: Alain Courteville, Congénies (FR); Christian Neel, Nîmes (FR); Charankumar Godavarthi, Nîmes (FR)

(73) Assignee: FOGALE NANOTECH, Nîmes (FR)

( * ) Notice: Subject to any disclaimer, the term of this patent is extended or adjusted under 35 U.S.C. 154(b) by 66 days.

(21) Appl. No.: 16/495,769

(22) PCT Filed: Mar. 12, 2018

(86) PCT No.: PCT/EP2018/056056
§ 371 (c)(1),
(2) Date: Sep. 19, 2019

(87) PCT Pub. No.: WO2018/172119
PCT Pub. Date: Sep. 27, 2018

(65) Prior Publication Data
US 2021/0080246 A1    Mar. 18, 2021

(30) Foreign Application Priority Data

Mar. 21, 2017    (FR) ...................................... 1752314

(51) Int. Cl.
*G01B 9/02*       (2006.01)
*A61B 5/00*       (2006.01)
(Continued)

(52) U.S. Cl.
CPC ........ *G01B 9/02091* (2013.01); *A61B 5/0066* (2013.01); *A61B 5/1075* (2013.01);
(Continued)

(58) Field of Classification Search
CPC ............ G01B 9/02091; G01B 9/02083; G01B 9/0209; G01B 11/0675; G01B 11/06; A61B 5/1075
See application file for complete search history.

(56) References Cited

U.S. PATENT DOCUMENTS 7,426,036 B2     9/2008  Feldchtein et al.
2009/0244547 A1  10/2009 Ozawa
(Continued)

OTHER PUBLICATIONS

French Search Report from French Patent Application No. 1752314, dated Sep. 28, 2017.
(Continued)

*Primary Examiner* — Jonathan M Hansen
(74) *Attorney, Agent, or Firm* — Greer, Burns & Crain, Ltd.

(57) ABSTRACT

A low-coherence interferometer apparatus for determining information on interfaces of an object including: a polychromatic light source; an optical system generating a measurement optical beam and a reference optical beam; a delay line introducing a variable optical delay between the optical beams; detection optics combining the beams, and producing a spectral signal representative of an optical-power spectral density of the resulting interference signal; a control and processing module acquiring a plurality of spectral signals for a plurality of optical delays, determining, for each spectral signal, optical retardation information between interfering beams within a spectral measurement range, analyse the variation in the retardations, and assign the optical retardation determined on the basis of the different spectral signals to interface curves, corresponding to straight lines with positive, negative, zero or almost-zero gradient, depending on the respective optical delay of the acquisition of the spectral signals, and to deduce information of the object.

16 Claims, 3 Drawing Sheets

(51) Int. Cl.
*A61B 5/107* (2006.01)
*G01B 11/06* (2006.01)
(52) U.S. Cl.
CPC ....... *G01B 9/0209* (2013.01); *G01B 9/02083* (2013.01); *G01B 11/06* (2013.01); *G01B 11/0675* (2013.01); *G01B 2210/56* (2013.01)

(56) References Cited

U.S. PATENT DOCUMENTS

| | | | |
|---|---|---|---|
| 2011/0157596 A1* | 6/2011 | Wax | A61B 5/0084 356/456 |
| 2011/0181889 A1 | 7/2011 | Kabetani et al. | |
| 2012/0257207 A1* | 10/2012 | Marx | G01B 11/06 356/451 |
| 2012/0320380 A1* | 12/2012 | Schonleber | G01B 11/2441 356/479 |
| 2014/0233016 A1* | 8/2014 | Aiyer | G01B 11/2441 356/51 |
| 2016/0038023 A1 | 2/2016 | Endo et al. | |
| 2017/0363418 A1* | 12/2017 | Ryu | G01B 11/0625 |
| 2018/0364028 A1 | 12/2018 | Piel et al. | |

OTHER PUBLICATIONS

International Search Report from International Patent Application No. PCT/EP2018/056056, dated May 8, 2018.

* cited by examiner

LOW-COHERENCE REFLECTOMETRY METHOD AND DEVICE EMPLOYING TIME-FREQUENCY DETECTION

BACKGROUND

The present invention relates to a low-coherence reflectometry device and method with time-frequency detection.

The field of the invention is more particularly, but non-limitatively, that of optical devices for measuring structures of objects, distances and thicknesses.

Different optical techniques are known, based on low-coherence interferometry, for measuring distances or thicknesses of materials or of internal structures. These techniques are generally known as optical coherence tomography (OCT) or optical coherence reflectometry (OCR).

Techniques are known based on time-domain detection (TD-OCR for time-domain OCR). A delay line introduces a variable delay between a reference beam and a measurement beam originating from the object to be measured. The two beams interfere on an intensity detector and produce interferograms when the delay between the measurement beam reflected in the object and the reference beam is shorter than the coherence length of the optical source. The position of the interferograms over the course of the delay line is representative of the position of the interfaces.

These techniques have the advantage that the measurement range is only limited with respect to large distances by the course of the delay line, and can easily achieve several tens of centimetres.

On the other hand, they have the drawback that the measurement rates are limited by the speed of displacement of the delay line, and as a result they are sensitive to vibrations. Moreover, they require the use of wide-spectrum optical sources emitting continuously, because of the high rate time sampling requirements of the interference signal. In fact, the pulsed or frequency scanning sources have repetition frequencies that are too slow and incompatible with the required time-sampling frequencies. Now, the continuous sources available in practice are limited in terms of spectral width, which limits the minimum measurable thicknesses.

Techniques are also known based on detection in the frequency or spectral domain. Light originating from reflections on interfaces of an object to be measured is directed towards a detector, which makes it possible to measure the intensity of the interference signals generated at a plurality of wavelengths. Sometimes, a reference beam is also used to define a position reference.

In particular, techniques are known based on a wide-spectrum light source and detection of the spectral type, with a detector of the spectrometer type that makes it possible to measure the luminous intensity received as a function of the optical wavelength (Frequency Domain OCR (FD-OCT)).

Techniques are also known based on a tunable or scanning wavelength laser source and intensity detection (Swept Source OCR (SS-OCT)).

In both cases, at the exit of the detector a measurement of the power spectral density of the light received is obtained that corresponds to the spectrum of the source, modulated depending on the contributions and differences in optical paths of the different reflections contributing thereto. Analysis of this spectrum, for example by Fourier transform, makes it possible to measure the thicknesses between the interfaces of the object, and/or to locate these interfaces.

The techniques with detection in the spectral domain have the advantage of allowing better measurement sensitivity than the techniques with detection in the temporal domain, and very fast measurement rates limited only by the measurement rates of the detectors. They also have the advantage of allowing the use of pulsed or scanning sources that make it possible to obtain greater spectral widths than continuous sources, and which thus make it possible to measure fine thicknesses.

However, they have the drawback that it can be difficult to interpret the measurements for objects with a complex structure, in particular because the distance measurements deduced from the power spectral density are unsigned values.

Moreover, the spectral techniques only allow a limited measurement range with respect to large distances, in particular with a signal-to-noise ratio which deteriorates towards large distances due to effects of sampling of the spectrum and the coherence length of the detected light.

Thus, for example, a squared spectrum source centred on a central wavelength $\lambda_0$ with a width $\Delta\lambda$ has a coherence length of the order of:

$$l_c = (\frac{1}{2})(\lambda_0^2/\Delta\lambda)$$

This coherence length defines the minimum measurable optical depth $L_{min}$.

In a spectral detection device with a spectrometer making it possible to acquire N measurement points in the range of wavelengths $\Delta\lambda$ (for example over N pixels of a linear sensor), or in a device using a tunable laser source making it possible to generate N different wavelengths in the range of wavelengths $\Delta\lambda$, the maximum measurable optical depth $L_{max}$ is:

$$L_{max} = (N/4)(\lambda_0^2/\Delta\lambda)$$

Thus, the measurement range of a spectral system corresponds to:

$$L_{max}/L_{min} = L_{max}/l_c = N/2$$

It is therefore directly limited by the number of measurement points of the spectrometer (or, with a tunable source, by the number of distinct wavelengths which can be generated).

In practice, spectrometers comprise sensors with a few hundreds of points, and the measurement ranges of the spectral systems are generally of the order of approximately one hundred times the coherence length of the source.

The TD-OCR or FD-OCR type techniques can be implemented in different forms. For example, the document U.S. Pat. No. 7,426,036 is known, which describes a device of the FD-OCR type. This device utilizes a Fizeau-type or common-path interferometer configuration which makes it possible to generate an optical reference beam in the same arm of the interferometer as the measurement beam. The reference beam is used to generate an optical reference from which the distances of the interfaces of the object to be measured are determined. It also comprises a delay line that makes it possible to set the position of the optical reference statically.

Among the existing sources that can be used for low-coherence interferometry, and in particular which can be effectively coupled in single-mode optical fibres, optical sources of the ASE (Amplified Spontaneous Emission) type or superluminescent diode (SDL) type are known. These sources allow continuous emission of light. They can therefore be utilized with techniques of the TD-OCR and FD-OCR type. However, they have the drawback of having a limited spectral width, for example less than 100 nm around 1310 nm, which corresponds to a minimum measurable optical depth (or in air) of the order of 10 μm.

Optical sources which make it possible to generate wider spectra, and which therefore have shorter coherence lengths, are also known. These sources make it possible to achieve finer minimum measurable thicknesses (for example of the order of 5 μm or less). However, they are either pulsed (such as supercontinuum laser sources that generate a wide spectrum by injecting light pulses originating from a laser in a highly non-linear medium such as a photonic crystal fibre) or scanning (tunable lasers), with repetition or scanning frequencies often of the order of a few kilohertz. They are therefore incompatible with signal acquisition frequency requirements of TD-OCR type detections, and are only used with spectral detection techniques.

Now, some industrial applications, in particular in the semiconductor industry, need to be able to measure both thicknesses of a few microns and optical distances of the order of a few millimetres, which requires a measurement range which cannot be achieved with the known systems.

An object of the present invention is to propose a device and a method for measuring distances and thicknesses which overcomes the drawbacks of the prior art.

An object of the present invention is also to propose such a device with an increased measurement range.

An object of the present invention is also to propose such a device that makes it possible to measure very small thicknesses or distances.

An object of the present invention is also to propose such a device that allows very precise measurements.

SUMMARY

This objective is achieved with a low-coherence interferometer device for determining information on the structure and/or the location of interfaces of an object, comprising:
  a polychromatic light source;
  an optical system for generating a measurement optical beam reflected by said object, and a reference optical beam;
  a delay line for introducing a variable optical delay between the measurement optical beam and the reference optical beam;
  an optical detection for combining the measurement optical beam and the reference optical beam, and producing a spectral signal representative of an optical-power spectral density of the resultant interference signal;
  characterized in that it also comprises a control and processing module arranged in order to:
  acquire a plurality of spectral signals for a plurality of optical delays;
  determine, for each spectral signal, optical delay information between interfering beams within a measurement range called spectral measurement range;
  analyze the evolution of said optical retardations, depending on the optical delay and assign the optical retardation or retardations determined from the different spectral signals to one or more so-called interface curves, corresponding to straight lines with positive, negative, zero or almost-zero gradient, depending on the respective optical delay of the acquisition of said spectral signals; and
  deduce therefrom information on the structure and/or the location of interfaces of the object.

The spectral measurement range can, of course, be expressed in time (optical retardation) or optical distances (path differences of the beams). It is recalled that the optical distances, the optical paths and the optical depths correspond to geometric distances multiplied by the refractive index of the media passed through.

Likewise, the optical delay introduced by the delay line can be expressed in time or optical distance.

Furthermore, the terms "optical retardation" or "optical delay" express differences in route time or time offsets between beams originating from the same source.

An interface curve can for example represent the evolution of an optical retardation linked to interferences between the reference optical beam and the measurement optical beam as reflected by a particular interface of the object depending on the optical delay.

According to embodiments, the device of the invention can comprise a light source emitting a polychromatic light in the form of pulses and an optical detector of the spectrometer type.

The light source can comprise, for example, a supercontinuum laser that emits light with a wide spectrum, for example in the visible and/or infrared spectrum.

The optical detector can comprise, for example, a dispersive element such as a grid or a prism making it possible to disperse the light spectrally, and a linear or matrix detector with a plurality of individual pixels or detectors making it possible to measure the luminous intensity separately for different wavelengths.

According to other embodiments, the device of the invention can comprise a light source of the tunable or scanning laser type, and an optical intensity detector.

In this case, the tunable or scanning laser emits a monochromatic light the wavelength of which varies over time, in order to produce a polychromatic source. The intensity received on the detector at each moment can be linked to the emission wavelength in order to reconstruct a power spectral density measurement.

According to embodiments, the device of the invention can comprise a delay line arranged so as to vary an optical path of the measurement optical beam, or of the reference optical beam or of both these two beams (for example in opposite directions).

According to embodiments, the device of the invention can comprise a delay line making it possible to introduce optical delays in discrete steps.

In this case the delays or variations in optical paths introduced by the delay line correspond to a set of discrete values.

The delay line can in particular comprise an optical switch.

This switch can for example make it possible to select optical paths of a determined length.

According to embodiments, the device of the invention can comprise a delay line making it possible to introduce a continuously variable optical delay.

According to embodiments, the device of the invention can comprise a Michelson interferometer.

According to other embodiments, the device of the invention can comprise a common-path interferometer with a measurement arm in order to direct the measurement beam towards the object, and a semi-reflective element inserted in said measurement arm in order to generate the reference optical beam.

The semi-reflective element can comprise any element suitable for generating a partial reflection of the incident beam. It can comprise, non-limitatively:
  an element generating a refractive index discontinuity between two portions of optical fibres;

a fibre-air interface at the end of the optical fibre;
an element such as a glass surface or a beam splitter inserted in a path of a beam freely propagating or in air.

The device can then comprise a differential delay line with an optical reflectivity at a fixed position, and the delay line.

This differential delay line can be arranged in order to introduce a variable optical retardation between the measurement optical beam and the reference optical beam originating from the measurement arm.

The device can also comprise a differential delay line with an optical reflectivity at a variable position, and the delay line.

According to another aspect, a method is proposed for determining information on the structure and/or the location of interfaces of an object implementing a low-coherence interferometer, comprising the steps of:
  emitting a polychromatic light with a polychromatic light source;
  generating a measurement optical beam reflected by said object to be measured, and a reference optical beam;
  introducing a variable optical delay between the measurement optical beam and the reference optical beam with a delay line;
  combining, by means of optical detection, the measurement optical beam and the reference optical beam and production of a spectral signal representative of an optical-power spectral density of the resulting interference signal;
  said method also comprising the steps of:
  acquiring a plurality of spectral signals for a plurality of optical delays;
  determining, for each spectral signal, optical retardation information between interfering beams within a measurement range called spectral measurement range;
  analyzing the evolution of said optical retardations depending on the optical delay, and assigning the optical retardation or retardations determined from the different spectral signals to one or more curves, called interface curves, corresponding to straight lines with positive, negative, zero or almost-zero gradient, depending on the respective optical delay of acquisition of said spectral signals; and
  deducing information on the structure and/or the location of interfaces of the object.

According to embodiments, the method of the invention can comprise acquiring a plurality of spectral signals for a plurality of optical delays within a range of optical delays making it possible to generate optical route equalities between the reference optical beam and the measurement optical beam when the object is within a measurement range called temporal measurement range.

The method of the invention can thus for example comprise the acquisition of a plurality of spectral signals for a plurality of optical path difference conditions between the reference optical beam and the measurement optical beam as reflected by a particular interface of the object, which correspond respectively to a path difference that is positive, then zero or almost zero, then negative (or vice-versa).

According to embodiments, the method of the invention can comprise the acquisition of a plurality of spectral signals for a plurality of optical delays spaced apart by an increment corresponding at most to half of the spectral measurement range.

This condition makes it possible to detect an optical retardation between same interfering beams at least twice, for two consecutive optical delay values.

Determining optical retardation information between interfering beams can comprise calculating a temporal interference signal and the determination of positions of interference peaks.

The temporal interference signal can be for example determined by using a Fourier transform, or an inverse Fourier transform.

According to embodiments, the method of the invention can comprise searching for interface curves corresponding to straight lines with positive or negative unitary gradient.

Such interface curves can represent in particular the evolution of an optical retardation linked to interferences between the reference optical beam and the measurement optical beam as reflected by a particular interface of the object, since the evolution of the optical retardation measured based on the spectral signals corresponds, plus or minus the absolute value, to the variation in the optical delay between the acquisition of these spectral signals.

According to embodiments, the structure and/or the location of interfaces of the object can be determined by using the interface curve or curves.

In particular, the structure and/or the location of interfaces of the object can be determined by determining the respective optical delay or delays for which the optical retardation along an interface curve is zero.

In fact, an optical delay that respects this condition corresponds to a condition for which there is an optical path equality between the reference optical beam and the measurement optical beam as reflected by a particular interface of the object. Knowledge of the optical delay makes it possible to locate this interface.

The interfaces of the object are thus located in terms of optical positions or distances. It is then possible to determine the actual (geometrical) positions or distances by taking account of the refractive indices of the environments passed through.

According to another aspect, an appliance is proposed comprising a device according to the invention, and/or implementing the method according to the invention.

An appliance according to the invention is in particular proposed for measuring distances and/or thicknesses of layers on an object comprising integrated electronic and/or integrated optical components and/or elements.

The object can be or comprise for example a wafer, and/or wafer elements, and/or any element originating from a manufacturing process of the microelectronics or micro-optics type.

Of course, the invention can also be utilized in order to carry out measurements on all types of objects of an industrial or biological nature.

An appliance according to the invention is also proposed for measuring distances and/or thicknesses of layers or layer structures on a biological object.

This object can be or comprise, for example, a biological tissue, a cell culture, skin, a blood vessel, etc.

BRIEF DESCRIPTION OF THE DRAWINGS

Other advantages and characteristics of the invention will become apparent on reading the detailed description of implementations and embodiments that are in no way limitative, and from the attached figures.

DETAILED DESCRIPTION

Figure 1:
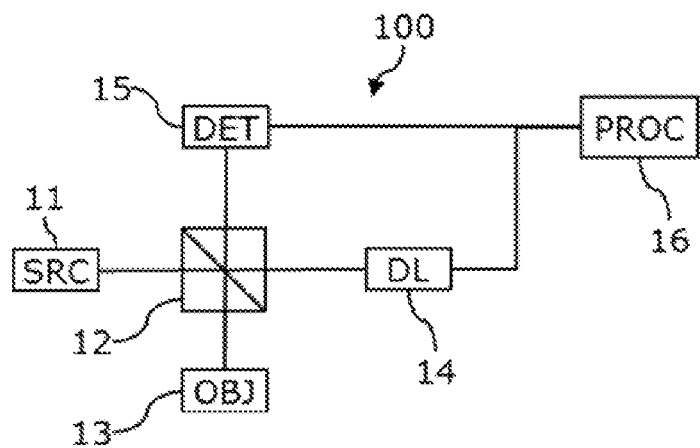
FIG. 1 shows a first embodiment of a device according to the invention.

It is well understood that the embodiments that will be described hereinafter are in no way limitative. Variants of the invention can in particular be considered comprising only a selection of characteristics described hereinafter in isolation from the other characteristics described, if this selection of characteristics is sufficient to confer a technical advantage or to differentiate the invention with respect to the state of the prior art. This selection comprises at least one, preferably functional, characteristic without structural details, or with only a part of the structural details if this part alone is sufficient to confer a technical advantage or to differentiate the invention with respect to the state of the prior art.

In particular, all the variants and all the embodiments described can be combined together if there is no objection to this combination from a technical point of view.

In the figures, elements common to several figures keep the same reference.

Firstly, a first embodiment of the device according to the invention will be described with reference to FIG. 1.

In this embodiment, the device 100 is produced in the form of a Michelson interferometer. It comprises a light source 11, a separator optical element 12, a time delay line 14, a detector 15 and a processor unit 16.

The light originating from the light source 11 is divided by the separator element 12 into a measurement beam directed towards the object 13 and a reference beam directed towards the delay line 14. After reflection respectively on the object 13 and in the delay line 14, these two beams are directed towards the detector 15 in order to measure the interferences thereof.

The device 100 as shown is produced with discrete optical components, with for example a separator optical element 12 in the form of a separator cube or a beam splitter, and freely propagating beams. It may of course be produced with any other kinds of technologies or combinations of technologies, by using for example optical fibres and/or planar guides on a substrate, and a separator optical element 12 in the form for example of an optical-fibre or planar Y-junction coupler.

The device 100 utilizes detection of the spectral type, which makes it possible to obtain at the exit of the detector 15 a spectral signal representative of a power spectral density of the optical signal incident on this detector 15.

In one configuration, the device 100 comprises a wide-spectrum light source 11, which can be either a source emitting light continuously (ASE, superluminescent diode), or a source emitting pulsed light (supercontinuum laser). In this configuration, the device 100 comprises a detector 15 of the spectral type (such as a spectrometer), with for example a dispersive element that makes it possible to spectrally disperse light on a linear or matrix detector so as to produce a measurement representative of an optical-power spectral density.

In another configuration, the device 100 comprises a tunable-wavelength light source 11, for example of the tunable or scanning laser type; thus the emission wavelength can be changed over time within a spectral range. In this configuration, the device 100 comprises an intensity detector 15 (such as a photodiode, etc.) which measures the total incident optical power. By varying the wavelength of the light source 11, a signal is obtained at the exit of the detector 15 that is representative of an optical-power spectral density as above.

The device 100 also comprises a delay line 14 that makes it possible to vary, in a known manner, the length of the optical path of the reference beam relative to that of the measurement beam, and thus to vary the optical delay or the difference in optical paths between the measurement and reference beams. The presence of this reference beam makes it possible to produce an optical reference from which the distances of the different interfaces of the object 13 are measured.

In one configuration, the device 100 comprises a delay line 14 that makes it possible to vary the optical delay or the optical path of the reference beam continuously over time. This configuration can be utilized with a wide-spectrum continuous-emission or pulsed light source 11.

In another configuration, the device 100 comprises a delay line 14 which makes it possible to vary the optical delay or the optical path of the reference beam in discrete steps or increments. This configuration can be utilized with all types of light sources 11.

In other configurations (not shown), the device 100 can comprise a delay line that makes it possible to vary the optical delay or the optical path of the measurement beam over time, continuously or in discrete steps or increments. In this case, the reference beam can be of fixed length, or also comprise a delay line. The delay line can be produced by any means, including displacing a measurement collimator, or the interferometer assembly with the separator optical element 12, with respect to the object.

As explained above, the invention makes it possible to carry out measurements of distances or thickness over large measurement ranges, while benefiting from the advantages of spectral detection, in particular in terms of sensitivity and availability of sources. To this end, a plurality of spectral signal measurements is carried out, for a plurality of optical delays or positions of the delay line. These spectral measurements are then combined by the processor unit 16, taking account of the position of the delay line 14 where they are carried out (and thus the optical delay introduced), in order to produce a measurement of the thicknesses and the respective positions of the layers of the object 13. This method of acquisition and processing is described in detail hereinafter.

A second embodiment of a device according to the invention will now be described, with reference to FIG. 2.

In this embodiment, the device 200 is produced in the form of a common-path or Fizeau interferometer, which allows effective implementation of the invention.

The device 200 is presented in an embodiment based on single-mode optical fibres. Of course, it can be produced with any type of components, for example free-propagation components, or with integrated or planar optical components, or a combination of some of these different techniques.

The device 200 can be implemented in the same configurations, in terms of combinations of light sources 11, detectors 15 and delay lines 14 as the device 100 presented with respect to FIG. 1.

The device 200 comprises an encoding coupler 23 (which can also be a circulator) that directs the light originating from the light source 11 to a measurement arm. This measurement arm comprises a measurement optical fibre 21 and a measurement collimator 22 making it possible to collimate or focus a measurement beam on the object 13.

The incident beam in the measurement optical fibre 21 is partially reflected at the level of the measurement collimator 22, for example by exploiting the Fresnel reflection at the end of the measurement fibre 21, in order to generate a reference beam. The reflection at the end of the fibre can also be adjusted by applying thereto a dielectric or metallic semi-reflective deposit.

The measurement beam as reflected by the object 13 and the reference beam are directed by the encoding coupler 23 to a decoding coupler 24. They are then directed to a differential delay line 240 with a fixed-length reference arm 28 terminated by a fixed reflective element 29 (constituted for example by a mirror or a reflective deposit placed at the end of the optical fibre) and a variable-length arm 25 with a delay line 14. Each of the measurement and reference beams is partially directed into the reference arm 28 and partially into the variable-length arm 25 of the differential delay line 240.

The reflected beams respectively in the reference arm 28 and in the variable-length arm 25 are then directed by the decoding coupler 24 towards the detector 15.

In the embodiment presented, the delay line 14 comprises a moveable reflective element 27 in the form of a moveable mirror 27, and a collimator 26 in order to collimate or focus the light originating from the optical fibre onto the moveable mirror 27. The moveable mirror 27 is displaced in translation, between a proximal position towards the collimator 26 and an opposite distal position, by a drive system with means (such as an optical rule) for accurately measuring the position thereof.

Depending on the configurations, the moveable mirror 27 can be displaced continuously or in discrete steps.

According to a variant, the fixed reflective element 29 can be produced by a partial reflection in the variable-length arm 25, such as for example a reflection at the end of the fibre at the level of the collimator 26 of the delay line 14. In this case, the two arms of the differential delay line 240 are merged.

The differential delay line 240 makes it possible to modulate or compensate for the differences in optical paths introduced between the measurement and reference beams in the measurement arm.

The embodiment of the device 200 presents advantages with respect to the simple Michelson interferometer of the device 100 shown in FIG. 1. In particular, the measurement and reference beams travel the same path in the measurement optical fibre 21, such that the length of this fibre and the disturbances that it undergoes do not affect the measurements.

The device 200 also makes it possible to carry out measurements of distances or thickness over large measurement ranges, while benefiting from the advantages of spectral detection, in particular in terms of sensitivity and availability of sources. To this end, a plurality of measurements of spectral signals is carried out, for a plurality of positions or optical delays of the delay line 14. These spectral signals are then combined by the processor unit 16, taking account of the position of the delay line 14 where they were carried out (or the corresponding optical delay), in order to produce a measurement of the thicknesses and of the respective positions of the layers of the object 13. This method of acquisition and processing is described in detail hereinafter.

Figure 2:
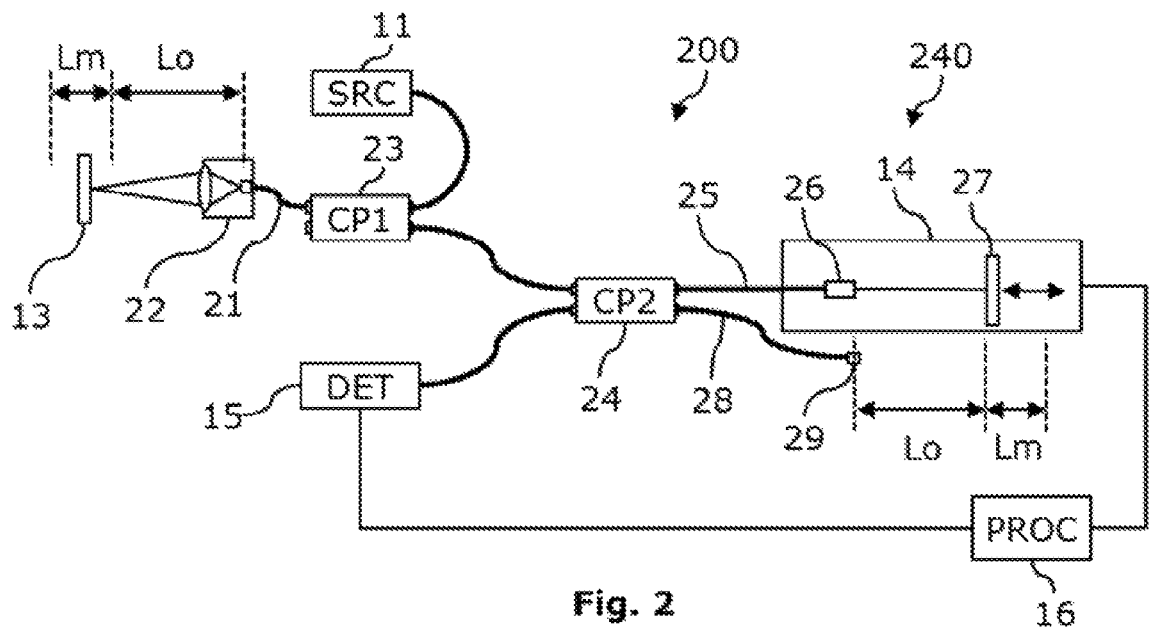
FIG. 2 shows a second embodiment of a device according to the invention.

According to variants, the devices 100 and 200 described above can comprise all types of delay lines 14 making it possible to generate optical delays or variants of optical paths, such as for example:
- a delay line based on a mechanical translation (or an oscillation) as shown in FIG. 2, which makes it possible to produce variations in optical paths that are continuous or in discrete steps;
- a delay line based on a rotation of a reflective element or of a transparent element, such as a parallel-face polygon inserted into the path of an optical beam, which makes it possible to produce variations in optical paths that are continuous or in discrete steps;
- a delay line based on a translation or a rotation of an element the shape of which makes it possible to vary an optical path depending on the displacement, continuously or in discrete steps;
- a delay line with a ladder portion comprising a succession of planar faces, parallel to one another, offset in the direction of the beam, which is displaced in a direction perpendicular to the beam so as to position the faces sequentially in front of the beam and thus produce variations in optical paths in discrete steps.

Figure 3:
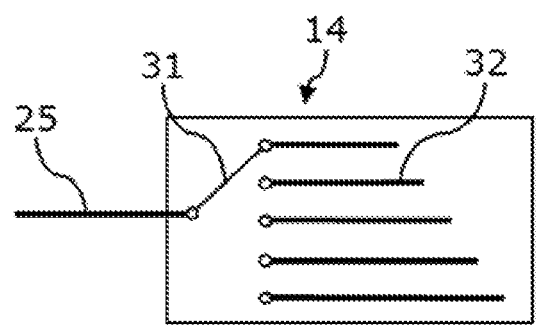
FIG. 3 shows an embodiment of a delay line that can be used in a device according to the invention.

FIG. 3 shows an embodiment of a delay line 14 making it possible to generate variations in optical paths or optical delays in discrete steps.

The delay line 14 comprises an optical switch 31 and a plurality of optical channels 32 of different length which reflect light at the end thereof. The optical switch 31 makes it possible to direct the incident light into a specific channel 32, so as to make it travel a path of determined length. By switching the selected channel, it is thus possible to change the optical path of the beam, or the corresponding optical delay.

Preferably, the optical switch 31 is a fibred component.

The optical channels 32 can be produced for example with optical fibres with a reflective termination.

The optical channels 32 can also be produced with planar waveguides on an optical substrate. This embodiment has the advantage of allowing accurate adjustment of the length of the optical channels by construction. The path thereof on the surface of the substrate can be adjusted so that they all terminate on a section of the substrate that is metallized in order to generate a reflection at the guide end.

The optical channels can also be produced with free propagation. In this case, each optical channel can comprise an optical fibre, a collimation lens and a reflector placed at the desired distance.

Figure 4:
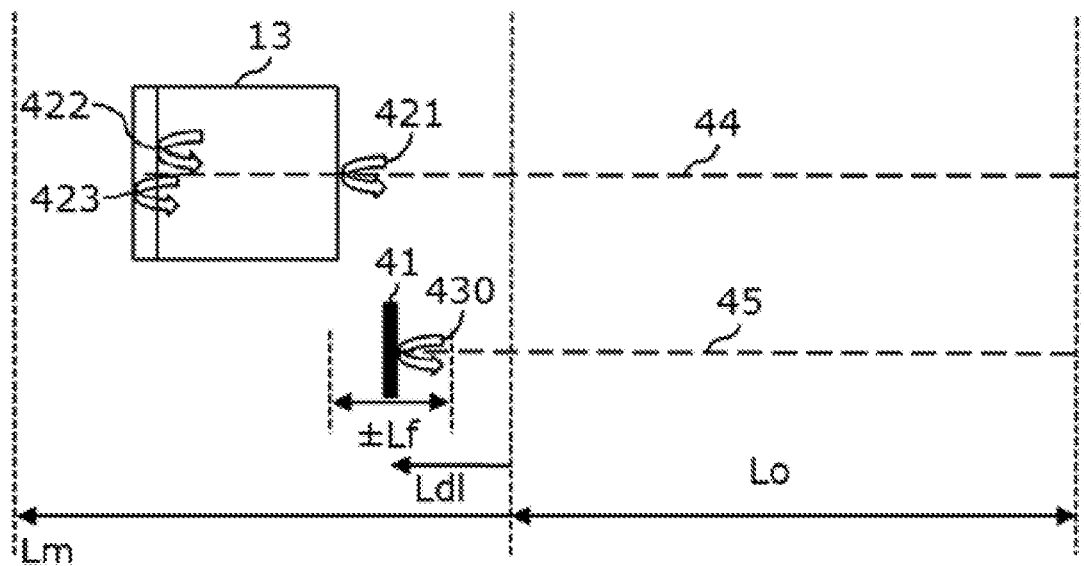
FIG. 4 shows the measurement principle of the invention.

FIG. 4 shows the measurement principle of the invention, such that it can be implemented for example with devices 100 and 200.

More specifically, FIG. 4 shows diagrammatically the lengths of the respective optical paths of a measurement beam 44 and of a reference beam 45, such that they propagate between the optical source 11 and the detector 15 in the devices 100 and 200.

In the example shown, the measurement beam 44 incident on an object 13 undergoes reflections 421, 422, 423 on the interfaces of the object. The reference beam 45 is reflected on an equivalent reference surface 41.

In the embodiments of the devices 100 and 200, the position of the equivalent reference surface 41 represents an optical path in the delay line 14.

In this representation, the delay line 14 makes it possible to introduce in the reference beam 45 an optical delay corresponding to an optical path Ldl which can vary between a value for example of zero (without loss of generality) and a maximum value Lm corresponding to the maximum course of the delay line. In the case of a delay line with a mirror 27 moveable in translation such as shown in FIG. 2, the optical path Ldl can be obtained by displacing the moveable mirror by a corresponding distance from the proximal position thereof.

In order to simplify the description, the optical paths or delays are only counted on an outward (or return) path of the beams, so as to correspond to the optical dimensions or displacements of the elements that generate the reflections. In practice, the measurement and reference beams travel outward and return paths, therefore double, but the fact of considering only half-paths does not change the equilibrium conditions.

More generally, the length of the reference optical path 45 is adjusted so as to be able to vary, depending on the displacement of the delay line, between a minimum distance called offset distance Lo and the maximum distance Lo+Lm, corresponding to the offset distance to which the course of the delay line is added. This range of optical distances between the offset distance Lo and the maximum distance Lo+Lm corresponds, for the measurement beam 44, to the temporal distance measurement range of the device, as it is only possible to obtain optical path equalities between the reference beam 45 and the measurement beam 44 for reflections on the object 13 taking place within this temporal distance measurement range.

Generally, the offset distance Lo can be defined with respect to an element separating the paths of the measurement and reference beams. It depends on the balancing of the different arms of the interferometer or interferometers.

For example, in the device 100, the offset distance Lo can be defined with respect to the separator element 12. It depends on the optical length of the reference arm, or in other words on the optical distance travelled by the reference beam between the separator element 12 and the time delay line 14.

In the device 200, the offset distance Lo can be defined with respect to the element that generates the reference beam in the measurement arm, at the level of the measurement collimator 21. It depends on the other hand on the difference in optical paths between the fixed-length reference arm 28 and the variable-length arm 25 of the differential delay line 240. In fact, as, explained above, each of the measurement and reference beams is separated into two components by the decoding coupler 24.

In the embodiment shown, the differential delay line 240 is balanced or arranged such that the optical path along the component of the reference beam reflected by the moveable mirror 27 up to the detector 15 can correspond to an optical path along a component of a measurement beam reflected by the fixed reflective element 29 which would be generated by a reflection on the object within the temporal distance measurement range of the device [Lo; Lo+Lm].

Alternatively, the differential delay line 240 can be balanced or arranged such that the optical path along the component of the reference beam reflected by the fixed reflective element 29 up to the detector 15 can correspond to an optical path along a component of a measurement beam reflected by the moveable mirror 27 which would be generated by a reflection on the object within the temporal distance measurement range of the device [Lo; Lo+Lm].

In the devices of the prior art that implement temporal detection, an interference peak (or an interference burst) would be obtained on the detector for each position of the delay line Ldl for which the optical path of the reference beam 45 up to the equivalent reference surface 41 corresponds to an optical path of the measurement beam 44 up to an interface of the object 13. Thus an interference peak would be obtained for each interface of the object 13 situated within the measurement range of temporal distances of the device [Lo; Lo+Lm]. The width of these interference peaks would depend on the coherence length of the source.

As explained previously, the invention utilizes spectral or frequential detection. A spectral signal representative of an optical-power spectral density is thus detected at the exit of the detector 15. This spectral signal depends on the spectrum of the source, and on the interferences between pairs of beams that are superimposed on the detector. By applying the Wiener-Khinchin theorem, it is possible to calculate an inverse Fourier transform of this spectral signal and thus obtain the autocorrelation function thereof in the temporal domain or by distance. Thus a temporal interference signal is obtained by optical distances or by optical retardations with an interference peak for each optical path difference or each optical retardation between pairs of incident beams on the detector, within an optical distance spectral measurement range Lf.

As explained above, this spectral measurement range corresponds, in optical distances, to the maximum at:

$$Lf\max = N/2l_c,$$

With $l_c$ the coherence length of the source and N the number of sampling points of the spectrum. It is thus directly limited by the number of measurement points of the spectrometer or, with a tunable source, by the number of distinct wavelengths that can be generated.

The spectral detection is not sensitive to the sign of the measured optical path differences. Therefore it only supplies the absolute value (or an unsigned value). Thus, for a position Ldl of the equivalent reference surface 41 (or an optical delay introduced by the delay line), the spectral detection supplies a measurement, in absolute value, of the optical path differences or of the optical retardations between the reference beam 45 and the reflections of the measurement beam 44 on interfaces of the object located at optical distances Lo+Ldl±Lf.

The spectral detection is also sensitive to optical path differences between reflections of the measurement beam. It therefore produces an ambiguous signal which is generally complex to analyze.

In order to resolve the ambiguities of sign and distinguish the interferences between reflections of the measurement beam 44 from those between the reference beam 45 and the measurement beam 44, a solution of the prior art consists of statically positioning the equivalent reference surface 41 such that the optical path differences between the reference beam 45 and the reflections of the measurement beam 44 on interfaces of the object 13 (or the corresponding optical retardations) all have the same sign, and a value greater than the thicknesses between layers of the object 13. This amounts to adjusting the delay line such that the optical paths along the measurement beam 44 up to the reflections 421, 422, 423 are all greater (or less) than the optical path along the reference beam 45 up to the reflection 430 on the equivalent reference surface 41. But this severely limits the usable distance measurement range, which corresponds at maximum to the optical distance spectral measurement range Lf.

The solution of the invention consists of acquiring a plurality of spectral measurements or spectral signals at a plurality of positions on the equivalent reference surface 41 corresponding to distances Ldl (or optical delays) comprised within the temporal distance measurement range of the device [Lo; Lo+Lm]. The structure of the object can then be determined unambiguously from curves called "interface curves" passed through by the interference peaks detected in the successively acquired spectral signals.

Figure 5:
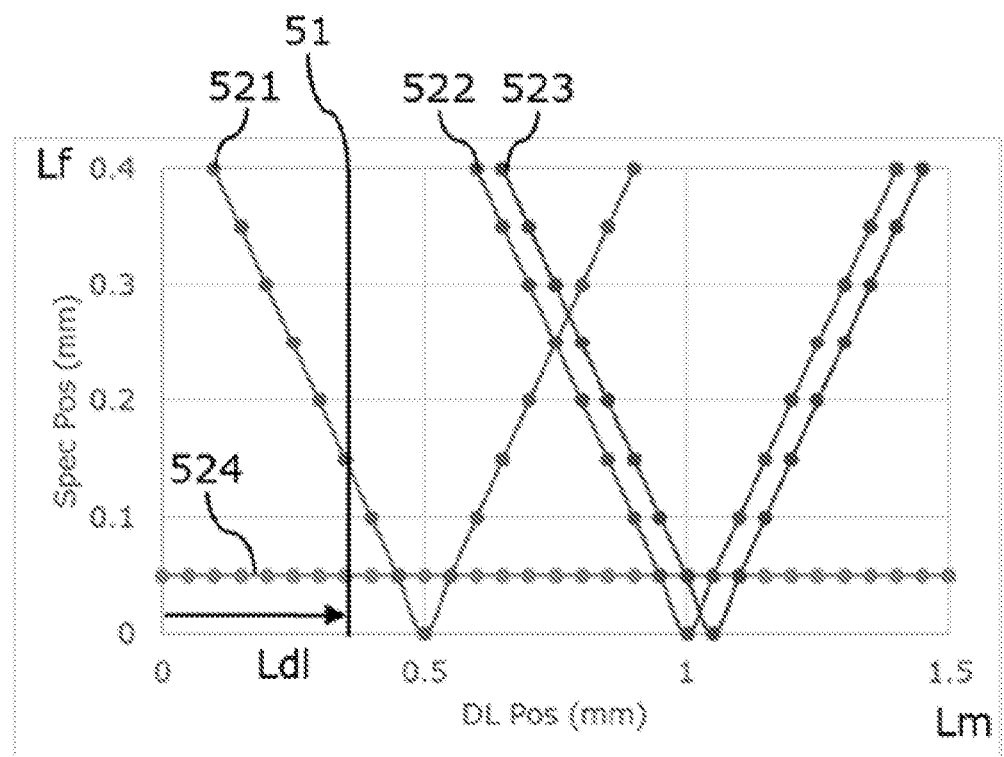
FIG. 5 shows an example of measurements obtained with the invention.

FIG. 5 shows examples of measurements obtained under these conditions, in the measurement configuration shown in FIG. 4.

The horizontal axis "DL Pos" corresponds to optical path differences (or the optical delays) generated by the delay line, or in the example shown in FIG. 4, to the position Ldl of the equivalent reference surface 41. The vertical axis "Spec Pos" corresponds to optical path differences (or optical retardations) obtained from spectral signals as measured by the spectral detector 15, within the measurement range of optical spectral distances Lf. Thus a diagram is constructed of spectral measurements vs. reference positions or optical delays.

As explained above, the position Ldl of the equivalent reference surface 41 is displaced within the temporal distance measurement range of the device [Lo; Lo+Lm] within which are located the interfaces of the object 13 according to a plurality of measurement positions 51 corresponding to optical delays of the delay line. For each of these measurement positions 51, a spectral signal measurement is carried out from which are deduced positions of interference peaks corresponding to optical retardation measurements.

The different optical retardations measured appear in the diagram of measurements of spectral signals vs. positions or optical delays in the form of interface curves the shape of which depends on the origin of the optical retardation.

Thus, for example, a thin layer the thickness of which is less than the range of spectral measurements Lf results in an interference peak 524, originating from the interference between the two reflections 422, 423 of the measurement beam 44, the position of which in the diagram is independent of the measurement position 51 of the equivalent reference surface 41.

Furthermore, when there is a difference in the optical paths between the measurement beam 44 reflected on an interface of the object 13 and the reference beam 45 less than the range of spectral measurements Lf, an interference peak is obtained the position of which in the diagram depends on the absolute value of the difference in optical paths (or of the corresponding optical retardation). For example, the interferences between the reflection 430 of the reference beam 45 on the reference surface and respectively, the reflections 421, 422, 423 of the measurement beam 44 on the interfaces of the object 13 result in interference peaks 521, 522, 523. These interference peaks thus appear on interface curves as a "V"-shape corresponding to straight lines of gradient ±1 in optical distances (or in optical retardations). These straight lines corresponding to an interface of the object are cut off at the origin of the spectral signals (zero position) or at the axis of the optical delays, which corresponds to the condition in which the equivalent reference surface 41 is at the same optical distance as the interface of the object. In other words, the position of the intersection between an interface curve or straight line and the axis of the optical delays corresponds to the optical delay for which there is an equality of optical path between the reference beam and the measurement beam reflected by the interface of the object corresponding to this interface curve.

It should be noted that it is not possible under these conditions to determine the structure of an object 13 in the general case, even within a proximity corresponding to the spectral measurement range Lf, with a single spectral measurement produced for a single optical delay or with an equivalent reference surface positioned at a single measurement position 51.

According to the invention, spectral measurements are carried out for a plurality of measurement positions 51 of the equivalent reference surface 41 (or positions or optical delays of the delay line) such that each interference peak or each measured optical retardation can be assigned to an interface curve in the form of a straight line. To this end, it is necessary for each interference peak to be detected at least twice along this straight line. This condition is respected provided that the position increment ΔLdl (or the corresponding difference in optical delay) between the successive measurement positions 51 of the equivalent reference surface 41 is less than or equal to half of the spectral measurement range Lf used.

Assigning interface peaks to the different interface curves or straight lines is simplified by the fact that the interference peaks of the object can only be located on gradients of +1, −1 or zero.

The interference peaks situated on straight lines with positive or negative gradients correspond to positions of the interface of the object measured relative to the positions of the equivalent reference surface 41. The sign of the gradient of the straight line indicates the sign of this difference in position. Thus, in the knowledge of the position of the equivalent reference surface 41 (or the corresponding optical delay) for each measurement point 51, it is possible to locate without ambiguity the corresponding position of the interface of the object within the temporal distance measurement range of the device [Lo; Lo+Lm].

The interference peaks situated on interface straight lines with zero gradients correspond to differences in interface positions of the object, but provide no information on the location of these interfaces. They must therefore be distinguished in order to avoid false detections. This discrimination can be carried out based on the gradient value thereof.

Figure 6:
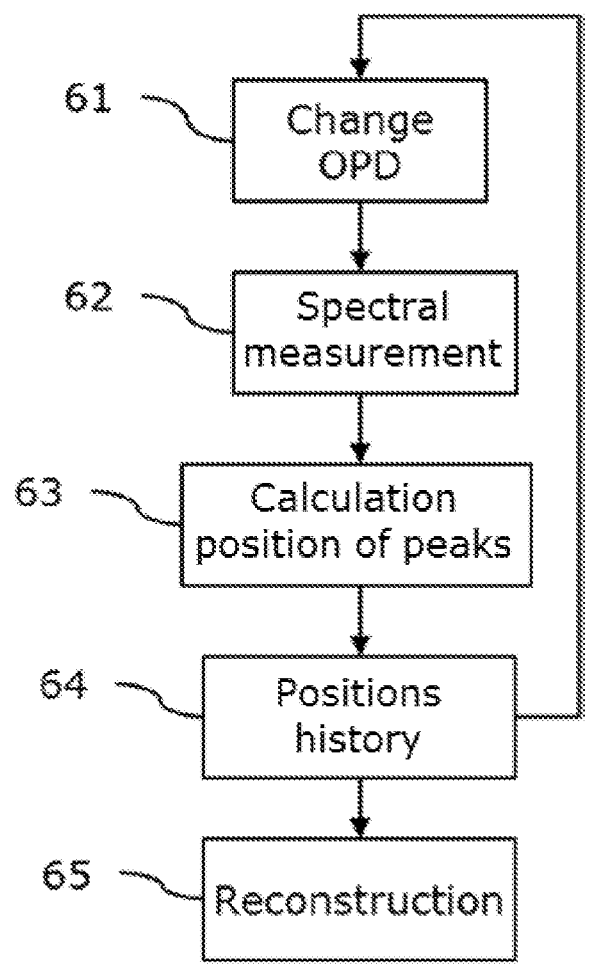
FIG. 6 shows a flow chart of the measuring method according to the invention.

FIG. 6 shows an example flow chart of the method according to the invention. It comprises:
  A step 61 of positioning the delay line in order to position the equivalent reference surface 41 at a known measurement position 51, corresponding to an optical delay value;
  A step 62 of acquiring a spectral signal;
  A step 63 of calculating the position of the interference peaks or of the corresponding optical retardations in the spectral signal;
  A step 64 of storing positions of interference peaks or corresponding optical retardations in a measurement history;
  A step 65 of reconstructing the structure of the object.

As explained above, the reconstruction step comprises assigning the positions of the interference peaks (or of the corresponding optical retardations) to interface curves, and/or constructing these interface curves.

To this end, for example, for each new measured spectral signal, an attempt is made to assign the detected interference peaks to existing straight lines (based on the distance of these peaks from these straight lines), and/or verify if it is possible to create new straight lines with these interference peaks and from the interference peaks detected during a previous spectral measurement and not assigned to a straight line.

Thus a set of interface straight lines or curves is obtained. In order to obtain the position of the interfaces of the object, it is possible for example to determine the position of the intersection of each interface straight line with a non-zero gradient with the temporal axis of the measurement positions 51 (or of the optical delays). As explained above, this intersection corresponds to the sought position of the interface (or to the corresponding optical retardation), Equally, or additionally, it is possible to determine the position on the temporal axis or of the optical delays of the intersection between two straight lines having an opposite gradient crossing on this axis and corresponding to one and the same interface.

The invention has the advantage of allowing a high degree of measurement accuracy. In fact, the position of each interface is determined from several measurements, which allows a significant improvement in the signal-to-noise ratio and uncertainty of measurement, both as regards the detection of the signal and the taking into account of the measurement uncertainties of the spectral detection and of the measurement of the position of the delay line.

Moreover, in particular when pulsed sources are used, thanks to the implementation of the spectral detection the device is not sensitive to the intensity noise of the source or to the variation in intensity from one pulse to another.

The invention also has the advantage of allowing devices to be produced with simultaneously:
- a large measurement range only achievable with temporal detection of the TD-OCR type, and
- a very fine minimum measurable thickness, made possible by the ability to utilize pulsed sources having a wider spectrum and greater power than could be achieved with continuous sources, or with scanning-frequency sources.

By way of non-limitative example, the invention can be implemented in order to produce an OCR type system that makes it possible to measure thicknesses and positions of interfaces of objects with a thickness or a maximum measurable optical distance of 10 mm, a thickness or a minimum measurable optical distance less than 5 µm, and a measurement rate of 100 Hz.

To this end, it is possible to utilize a device 100 or 200 according to the invention with:
- a light source 11 of the supercontinuum laser type that produces a light with a spectrum width greater than 200 nm around 1310 nm, in the form of nanosecond pulses with a repetition frequency of the order of 10 KHz;
- a delay line 14 with a mirror in oscillating linear displacement over a course of 10 mm at 50 Hz, i.e. a displacement at an average speed of 1 m/s;
- an optical detector 15 with a dispersive element and a linear sensor.

Under these conditions, the light source has a coherence length less than 5 µm, and thus makes it possible to achieve minimum measurable thicknesses or optical distances less than 5 µm. As explained above, the optical detector makes it possible to measure thicknesses or optical distances within a spectral measurement range extending from 5 µm to 500 µm. On the assumption that a spectral signal is acquired for each pulse of the source, i.e. at a frequency of 10 KHz, a spectral signal is obtained every 100 µm of displacement of the delay line. And thus each interface of the object can be potentially detected up to five times in five consecutive spectral signals, this in the entire course of the delay line, i.e. 10 mm.

It should be noted that such a measurement range of 5 µm to 10 mm cannot be achieved by a spectral system (FD-OCT or SS-OCT) of the prior art due to the spectrum sampling requirements and the limitations on coherence length of the source.

Furthermore, a maximum measurable optical depth of 10 mm can be achieved with a temporal system of the TD-OCR type of the prior art. However, for sampling the temporal interference signal with a delay line that is displaced in the example herein at 1 m/s, it is necessary to use a sampling frequency of 15 MHz or more in order to obtain of the order of 10 points per fringe at a wavelength of 1310 nm. A continuous source is therefore necessary. Now, the available sources such as superluminescent diodes (SLD) have at best a spectral width of the order of 100 nm to 1310 nm, and do not make it possible to achieve minimum measurable optical depths less than 10 µm, which remains insufficient.

Of course, the invention is not limited to the examples that have just been described, and numerous modifications may be made to these examples without exceeding the scope of the invention.

The invention claimed is:

1. A low-coherence interferometer device for determining information on the structure and/or the location of interfaces of an object, the device comprising:
    a polychromatic light source;
    an optical system for generating a measurement optical beam reflected by said object, and a reference optical beam;
    a delay line for introducing a variable optical delay between the measurement optical beam and the reference optical beam;
    an optical detector for combining the measurement optical beam and the reference optical beam and producing a spectral signal representative of an optical-power spectral density of the resulting interference signal;
    a control and processing module arranged to:
    acquire a plurality of spectral signals for a plurality of optical delays;
    determine, for each spectral signal, optical retardation information between interfering beams within a measurement range called spectral measurement range;
    analyze the evolution of said optical retardations depending on the optical delay and assign the optical retardation or retardations determined from the different spectral signals to one or more curves called interface curves defined entirely by straight lines having positive, or negative unitary, constant gradients, or zero gradients, depending on the respective optical delay of the acquisition of said spectral signals; and
    deduce therefrom information on the structure and/or the location of interfaces of the object by using the interface curve or curves.

2. The device of claim 1, which comprises a light source emitting a polychromatic light in the form of pulses and an optical detector of the spectral type.

3. The device of claim 1, which comprises a light source with a tunable or scanning laser, and an intensity optical detector.

4. The device of claim 1, which comprises a delay line making it possible to introduce optical delays in discrete steps.

5. The device of claim 4, in which the delay line comprises an optical switch.

6. The device of claim 1, which comprises a delay line making it possible to introduce a continuously variable optical delay.

7. The device of claim 1, which comprises a common-path interferometer with a measurement arm in order to direct the measurement beam towards the object, and a semi-reflective element inserted in said measurement arm in order to generate the reference optical beam.

8. The device of claim 7, which comprises a differential delay line with optical reflectivity at a fixed position, and the delay line.

9. A method for determining information on the structure and/or the location of interfaces of an object utilizing a low-coherence interferometer, the method comprising the steps of:
- emitting a polychromatic light with a polychromatic light source;
- generating a measurement optical beam reflected by said object to be measured, and a reference optical beam;
- introducing a variable optical delay between the measurement optical beam and the reference optical beam with a delay line;
- combining, by means of optical detection, the measurement optical beam and the reference optical beam and producing a spectral signal representative of an optical-power spectral density of the resulting interference signal;
- acquiring a plurality of spectral signals for a plurality of optical delays;
- determining, for each spectral signal, optical retardation information between interfering beams within a measurement range called spectral measurement range;
- analyzing the evolution of said optical retardations depending on the optical delay and assignment of the optical retardation or retardations determined from the different spectral signals to one or more curves, called interface curves, defined entirely by straight lines having positive, or negative unitary, constant gradients, or zero gradients, depending on the respective optical delay of acquisition of said spectral signals; and
- deducing information on the structure and/or the location of interfaces of the object by using the interface curve or curves.

10. The method of claim 9, which comprises acquiring a plurality of spectral signals for a plurality of optical delays within a range of optical delays making it possible to generate optical route equalities between the reference optical beam and the measurement optical beam when the object is located within a measurement range called temporal measurement range.

11. The method of claim 9, which comprises acquiring a plurality of spectral signals for a plurality of optical delays spaced apart by an increment corresponding at most to half of the spectral measurement range.

12. The method of claim 9, in which determining optical retardation information between interfering beams comprises calculating a temporal interference signal, and determining positions of interference peaks.

13. The method of claim 9, in which the structure and/or location of interfaces of the object is determined by determining the respective optical delay or delays for which the optical retardation along an interface curve is zero.

14. An appliance comprising a device according to claim 1, implementing a method for determining information on the structure and/or the location of interfaces of an object utilizing a low-coherence interferometer, comprising the steps of:
- emitting a polychromatic light with a polychromatic light source;
- generating a measurement optical beam reflected by said object to be measured, and a reference optical beam;
- introducing a variable optical delay between the measurement optical beam and the reference optical beam with a delay line;
- combining, by means of optical detection, the measurement optical beam and the reference optical beam and producing a spectral signal representative of an optical-power spectral density of the resulting interference signal;
- acquiring a plurality of spectral signals for a plurality of optical delays;
- determining, for each spectral signal, optical retardation information between interfering beams within a measurement range called spectral measurement range;
- analyzing the evolution of said optical retardations depending on the optical delay and assignment of the optical retardation or retardations determined from the different spectral signals to one or more curves, called interface curves, corresponding to straight lines having positive, or negative unitary gradients, or zero gradients, depending on the respective optical delay of acquisition of said spectral signals; and
- deducing information on the structure and/or the location of interfaces of the object by using the interface curve or curves.

15. The appliance according to claim 14, comprising measuring distances and/or thicknesses of layers on an object comprising components and/or elements of integrated electronics and/or integrated optics.

16. The appliance according to claim 14, comprising measuring distances and/or thicknesses of layers or layer structures on a biological object.

* * * * *